(12) United States Patent
Nam et al.

(10) Patent No.: US 12,427,167 B2
(45) Date of Patent: Sep. 30, 2025

(54) METHOD FOR PREPARING METAL NANOCUBE WITH CONTROLLED CORNER SHARPNESS INDEX

(71) Applicants: SEOUL NATIONAL UNIVERSITY R&DB FOUNDATION, Seoul (KR); BIONANO HEALTH GUARD RESEARCH CENTER, Daejeon (KR)

(72) Inventors: Jwa-Min Nam, Seoul (KR); Jeong-Eun Park, Seoul (KR); Yeon Hee Lee, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 1218 days.

(21) Appl. No.: 15/733,420

(22) PCT Filed: Jan. 25, 2019

(86) PCT No.: PCT/KR2019/001057
§ 371 (c)(1),
(2) Date: Jul. 23, 2020

(87) PCT Pub. No.: WO2019/147056
PCT Pub. Date: Aug. 1, 2019

(65) Prior Publication Data
US 2021/0161952 A1 Jun. 3, 2021

(30) Foreign Application Priority Data

Jan. 26, 2018 (KR) .......................... 10-2018-0010219
Oct. 17, 2018 (KR) .......................... 10-2018-0124004

(51) Int. Cl.
B22F 1/054 (2022.01)
A61K 33/242 (2019.01)
(Continued)

(52) U.S. Cl.
CPC ........ *A61K 33/242* (2019.01); *A61K 49/0093* (2013.01); *B22F 1/054* (2022.01);
(Continued)

(58) Field of Classification Search
None
See application file for complete search history.

(56) References Cited

FOREIGN PATENT DOCUMENTS

| KR | 10-2008-0069058 | 7/2008 |
|---|---|---|
| KR | 10-2012-0056024 | 6/2012 |

(Continued)

OTHER PUBLICATIONS

Wu et al. "Seed Mediated Synthesis of Gold Nanocrystals . . . " Langmuir. 26 (14), 12307-12313. (2010). (Year: 2010).*
(Continued)

*Primary Examiner* — Sheng H Davis
(74) *Attorney, Agent, or Firm* — HOVEY WILLIAMS LLP

(57) ABSTRACT

A method for preparing a metal nanocube with a controlled corner sharpness index includes a step of reacting with a first surfactant and a predetermined surface-protecting agent. A method for preparing a metal nanocube aggregate having a purity of 95% or more includes a step of centrifuging in the presence of a second surfactant. A probe composition includes the metal nanocube or metal nanocube aggregate prepared by the method; and a gold (Au) nanocube having an average edge length of 20 nm or less.

3 Claims, 13 Drawing Sheets

(51) Int. Cl.
*A61K 49/00* (2006.01)
*B22F 1/07* (2022.01)
*B22F 9/24* (2006.01)
*C09K 11/58* (2006.01)
*G01N 21/64* (2006.01)
*G01N 21/65* (2006.01)

(52) U.S. Cl.
CPC .............. *B22F 1/0553* (2022.01); *B22F 1/07* (2022.01); *B22F 9/24* (2013.01); *C09K 11/58* (2013.01); *B22F 1/056* (2022.01); *B22F 2301/255* (2013.01); *B22F 2304/054* (2013.01); *B22F 2304/056* (2013.01); *G01N 21/64* (2013.01); *G01N 21/658* (2013.01)

(56) References Cited

FOREIGN PATENT DOCUMENTS

| KR | 10-2014-0027786 | 3/2014 | |
|---|---|---|---|
| KR | 10-2015-0096187 | 8/2015 | |
| KR | 10-2015-0133873 | 12/2015 | |
| KR | 10-2016-0084064 | 7/2016 | |
| WO | WO-2016200525 A1 * | 12/2016 | ............ B22F 1/0018 |

OTHER PUBLICATIONS

Canepa et al. "Influence of Cetyltrimethylammonium Bromide . . . " J. Phys. Chem C. 122, 2350-2357 (2018). (Year: 2018).*
Xiao et al. "Surfatant-assisted, shape-controlled . . . ". Nanoscale, 3, 1383. (2011). (Year: 2011).*
Wu et al., "Seed-Mediated Synthesis of Gold Nanocrystals with Systematic Shape Evolution from Cubic to Trisoctahedral and Rhombic Dodecahedral Structures," Langmuir Article, American Chemical Society, vol. 26, Issue. 14, Jun. 17, 2010 pp. 12307-12313.
Zhang et al., "Individual Au-Nanocube Based Plasmonic Nanoprobe for Cancer Relevant MicroRNA Biomarker Detection," ACS Sens., vol. 2, 2017, pp. 1435-1440.
Zheng et al., "Successive, Seed-Mediated Growth for the Synthesis of Single-Crystal Gold Nanospheres with Uniform Diameters Controlled in the Range of 5-150 nm," Particle & Particle System Characterization, Wiley-VCH Verlag GmbH & Co. KGaA, Weinheim, vol. 31, 2014, pp. 266-273.

* cited by examiner

FIG. 5a
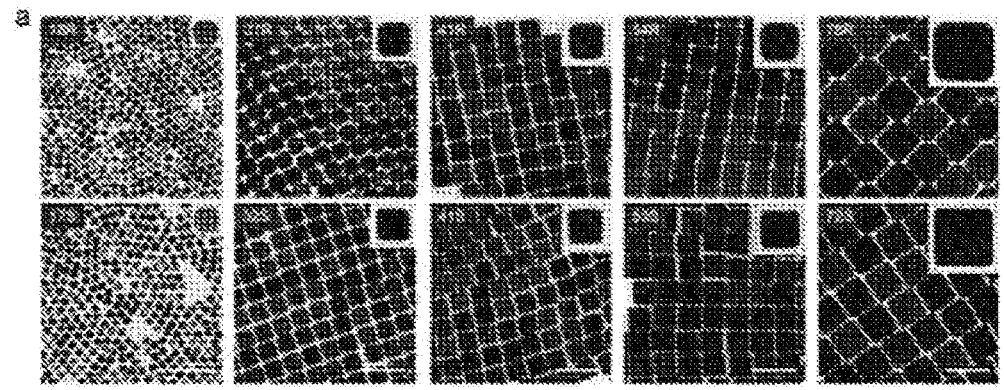
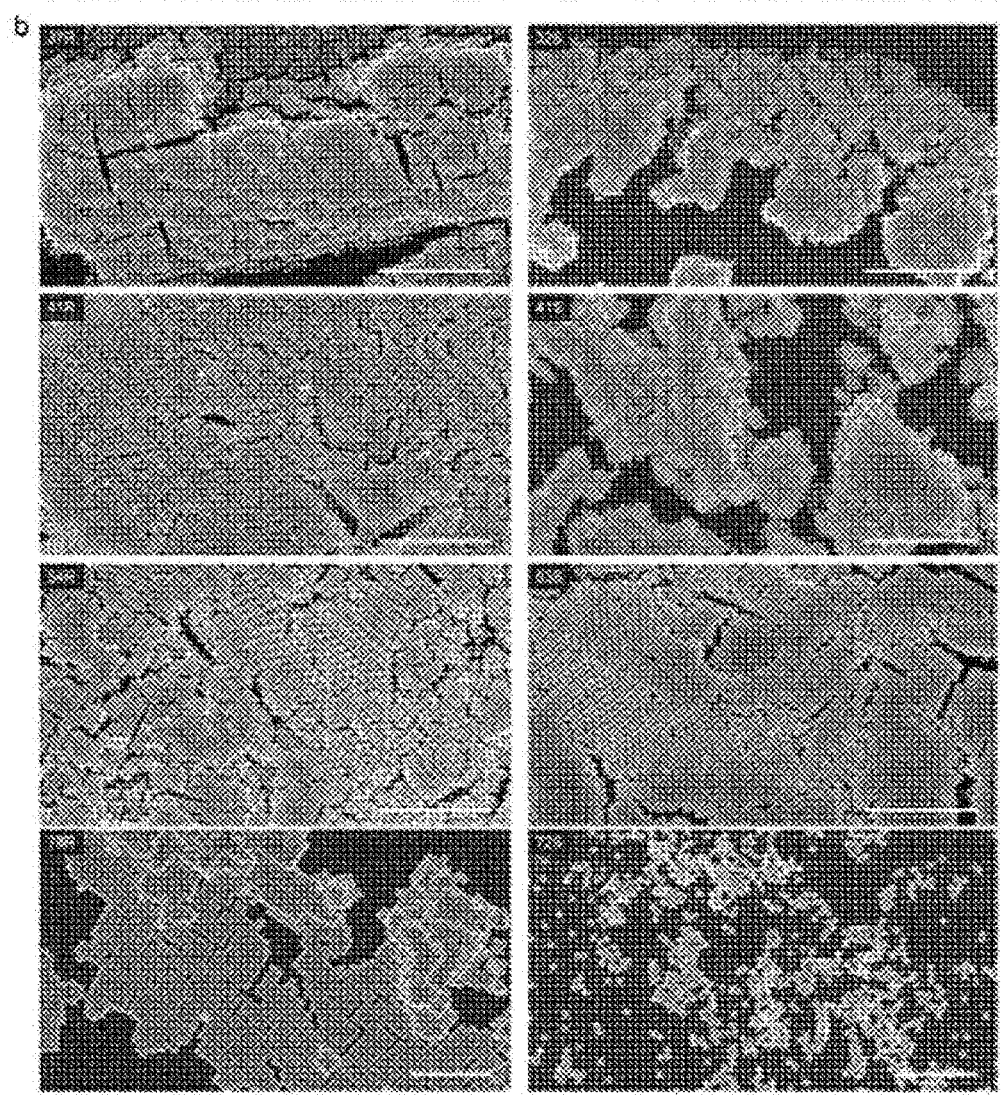
FIG. 5b

FIG. 11a
FIG. 11b
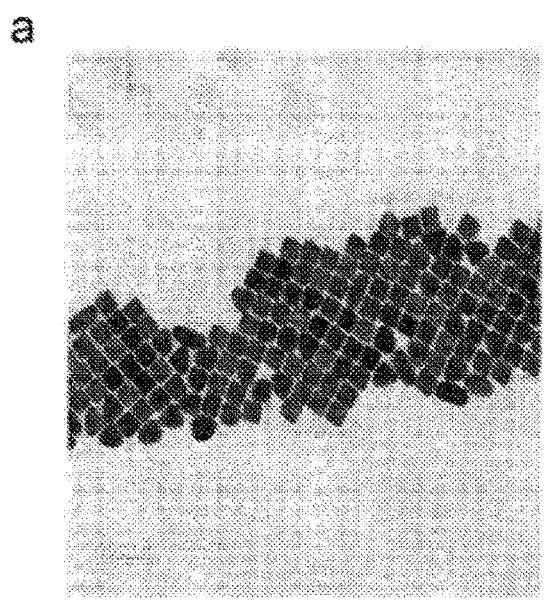
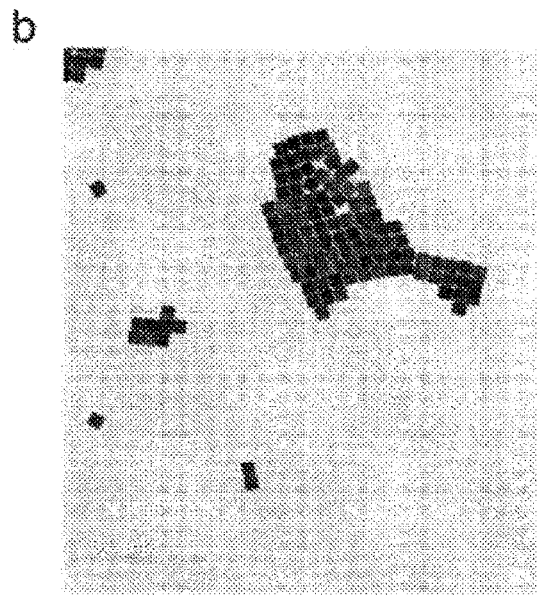

and furthermore, by performing a subsequent step of adding a surfactant to the solution in which the high-purity particles are dispersed, it is possible to finally obtain highly pure nanocubes in which all of the size, shape, and corner sharpness are uniform.

METHOD FOR PREPARING METAL NANOCUBE WITH CONTROLLED CORNER SHARPNESS INDEX

TECHNICAL FIELD

The present invention relates to a method for preparing a metal nanocube with a controlled corner sharpness index, comprising a step of reacting with a first surfactant and a predetermined surface-protecting agent; a method for preparing a metal nanocube aggregate having a purity of 95% or more, comprising a step of centrifuging in the presence of a second surfactant; a probe composition comprising the metal nanocube or metal nanocube aggregate prepared by the methods above; and a gold (Au) nanocube having an average edge length of 20 nm or less.

BACKGROUND ART

Localized surface plasmon resonance (LSPR) is a unique feature of plasmonic nanostructures that enables its application in various areas including sensing, bioimaging, therapeutics, nonlinear optics, and catalysis. Since it is primarily affected by the size and shape of plasmonic nanostructures, numerous studies have been conducted on precise structural control. Basic nanostructures (e.g., gold nanospheres and gold nanorods) have been extensively studied for several decades. For example, in order to produce ultra-smooth and highly spherical gold spheres, a cyclic process of growth and oxidative etching has been developed. In addition, methods of controlling the aspect ratio and facet morphology of gold nanorods have been attempted to acquire proper LSPR suitable for the areas to be applied. For gold nanocubes (AuNCs), which are known to show an enhanced plasmonic property due to the edges and perpendicular surfaces thereof, concave AuNC and tetrahexahedron structures were prepared, but a flexible size and sharpness control have not been realized. Methods for synthesizing AuNCs based on the seed-mediated growth reaction have been proposed, but their low reproducibility was shown to inhibit effective and practical utilization of AuNCs. The low reproducibility could be partly resolved by universal gold nanoparticle seeds acquired through iterative oxidative dissolution and a re-growth reaction. However, their intricate and time-consuming seed-preparation process makes facile synthesis of AuNCs difficult.

SUMMARY

The present inventors have made extensive efforts to discover a facile and feasible method capable of high-yield preparation of metal nanocubes with precisely controlled sizes and shapes, particularly the corner sharpness index. As a result, they have confirmed that precise shape control is possible by the modification of growth kinetics through fine-tuning of surface-protecting agents; that metal nanocubes can be obtained in a high yield of 95% or higher by refinement through a brief aggregation step in a shape-selective manner; and that such metal nanocube structures prepared with a precisely controlled shape enable the modulation of optical properties to be used for applications in various areas, thereby completing the present invention.

The present invention relates to a method for preparing a metal nanocube with a controlled corner sharpness index (hereinafter, CSI), comprising:

a step of determining the amount of a surface-protecting agent, in which the amount of the surface-protecting agent to be added in a step of preparing a mixed aqueous solution below is determined based on a surface area and a CSI of the metal nanocube to be finally prepared;

a step of preparing the mixed aqueous solution, in which a first surfactant, the surface-protecting agent in an amount determined according to the step of determining an amount of the surface-protecting agent, and metal nanoparticles with an average diameter of 3 nm to 30 nm are mixed to prepare the mixed aqueous solution; and a step of adding a metal ion precursor, in which the mixed aqueous solution is reacted by adding a reducing agent and a precursor solution comprising metal ions thereto, wherein the metal is gold (Au), silver (Ag), palladium (Pd), platinum (Pt), copper (Cu), aluminum (Al lead (Pb), or a combination thereof.

Another aspect of the present invention provides a method for preparing a metal nanocube aggregate with a purity of 95% to 99.9%, comprising:

a step of performing centrifugation and redispersion, in which a solution comprising metal nanocubes is centrifuged, and the precipitate is recovered and redispersed in another solution; and a step of adding a second surfactant and performing centrifugation, in which the second surfactant is added to the redispersed reaction solution and the mixture is centrifuged.

Still another aspect of the present invention provides a probe composition comprising the metal nanocube prepared by the above methods; or the metal nanocube aggregate prepared by the above methods.

Still another aspect of the present invention provides gold (Au) nanocubes in which each gold nanocube has an average edge length of 20 nm or less.

Hereinafter, the present invention is described in detail.

The present invention is based on the discovery that in the case of growing, as seeds, metal nanoparticles with an edge length of about 10 nm to nanocubes with an edge length ranging from a small size of the order of around 10 to 20 of nm to a large size of a few hundred nm, when a small amount of NaBr is added as a surface-protecting agent so as to provide bromide ions along with a sufficient amount of a surfactant, the shape of the edge of the nanocubes that are finally formed (e.g., degree of sharpness or roundness) can be controlled. Specifically, with respect to the amount of bromide ions required at this time, it was found that when the bromide ions were added in multiples within a specific range in proportion to the surface areas of the finally formed nanocubes, nanocubes with sharp edges were formed, whereas when the bromide ions were added in multiples outside the specific range, nanocubes with round edges were formed, and furthermore, when an excess amount of the bromide ions was added above the specific range, the nanocubes did not grow into an uniform form of particles, and instead, a mixture of various types of particles was formed.

In addition, the present invention is characterized by the discovery that with respect to the particles prepared in uniform sizes and shapes as described above, when the particles were dispersed in a surfactant solution and centrifuged, the spaces between the particles of the same size and shape were compressed by osmotic pressure, thus resulting in inter-particle aggregation. Accordingly, by using the above phenomenon, it is possible to refine the particles with deviation within 10% in size and corner sharpness to have a high purity of 95% or more.

In the present invention, the corner sharpness index (CSI) shown in Equation 1 below refers to a value defined by the edge length (EL) and the corner radius (CR) of nanocubes to be prepared, and it is a measure of the shape of the edge of nanocubes, specifically the sharpness or roundness of the edge. As the edge becomes sharper, the CIS value gets closer to 1.

$$CSI \equiv \frac{EL - 2CR}{EL} \quad \text{Equation 1}$$

In Equation 1 above, EL may be defined as the shortest distance from one point on a flat surface of a metal nanocube to another surface parallel thereto; and CR as the radius of a circle that perfectly matches a corner curvature.

The metal used in the metal nanocube of the present invention may be, for example, a noble metal. The metal may be a material showing localized surface plasmon resonance (LSPR). The metal may be gold (Au), silver (Ag), palladium (Pd), platinum (Pt), copper (Cu), aluminum (Al), lead (Pb), or a combination thereof, but is not limited thereto. Specifically, the metal may be Au, Ag, Pd, Pt, Cu, or a combination thereof. In embodiments of the present invention, metal nanocubes (i.e., AuNCs) were prepared using Au, which is a representative noble metal.

In the preparation method of the present invention, as the seed particles, metal nanoparticles having an average diameter of 3 nm to 30 nm may be used. Specifically, the average diameter of the metal nanoparticles may be in a range of 5 nm to 30 nm, or 6 nm to 30 nm, and more specifically 5 nm to 15 nm or 6 nm to 15 nm. As the metal nanoparticles, for example, gold nanospheres capped with CTAC may be used, but the metal nanospheres are not limited thereto. Furthermore, as the metal nanoparticles, commercial metal nanoparticles may be purchased and used as they are or after surface modification, or the metal nanoparticles may be prepared and used from smaller particles (e.g., particles having a size of 1 nm to 2 nm) using nanoparticle synthesis methods known in the art, but the metal nanoparticles to be used in the present invention are not limited thereto.

As used herein, the term "surface-protecting agent" may refer to a material which can selectively bind to a specific surface of a metal nanocube so as to control its crystal growth on a corresponding surface, thus making it capable of controlling the shape of the final product. For example, the surface-protecting agent may be an organic or inorganic salt of bromine providing bromide ions, which binds specifically to a (100) facet of a metal nanocube so as to control its crystal growth from a corresponding surface, thus making it capable of controlling the shape and corner sharpness of the particles to be finally formed. The chemical species of the surface-protecting agent is not limited as long as it can provide bromide ions quantitatively in a reaction solution. Specifically, the surface-protecting agent may be an organic salt of bromine (e.g., hexadecyltrimethylammonium bromide (CTAB), etc.) or a metal salt of bromine (e.g., NaBr, KBr, $MgBr_2$, and $CaBr_2$), but the surface-protecting agent is not limited thereto.

As used herein, the term "first surfactant" may refer to a molecule capable of preventing aggregation of metal nanoparticles used as seeds in a reaction solution. For example, the first surfactant may be hexadecyltrimethylammonium chloride (CTAC), but the first surfactant is not limited thereto, and any surfactant known in the art may be used without limitation as long as it can play the role of the first surfactant defined above. However, in the present invention, bromide ions are used as a surface-protecting agent; therefore, for the precise control of the concentration of bromide ions in a reaction system, it may be desirable that reactants other than the surface-protecting agent do not contain bromide ions. Therefore, in the present invention, a surfactant not containing bromide ions may be used as the first surfactant.

As used herein, the term "reducing agent" may refer to a reagent capable of reducing metal ions to grow crystals. For example, the reducing agent may be ascorbic acid, but is not limited thereto.

The precursor solution containing metal ions may be an aqueous $HAuCl_4$ solution, but is not limited thereto.

The method of the present invention for preparing a nanocube may further comprise: a step of performing centrifugation and redispersion, in which the reaction solution according to the step of adding the precursor comprising metal ions is centrifuged, and the precipitate is recovered and redispersed in another solution; and a step of adding a second surfactant and performing centrifugation, in which the second surfactant is added to the redispersed reaction solution and the mixture is centrifuged. By a refinement through the above additional steps, the metal nanocube with deviation in a CSI value controlled to be within ±10% can be provided at a purity of 95% or higher.

The metal nanocube prepared by the method of the present invention is characterized in that not only is its corner sharpness controlled, but also, its size (i.e., edge length) is uniform. Therefore, through the above additional refinement process, a metal nanocube with deviation in an edge length controlled to be within ±10% can be provided at a purity of 95% or higher.

For example, the metal nanocube prepared by the method of the present invention is one in which both a CSI value and an edge length are uniformly controlled. Therefore, through the additional refinement process described above, a metal nanocube with deviation both in a CSI value and an edge length controlled to be within ±10% can be provided at a purity of 95% or higher.

In the step of performing centrifugation and redispersion, a third surfactant may be further included so as to prevent aggregation of particles, but the step is not limited thereto. As the third surfactant, hexadecyltrimethylammonium bromide (CTAB) may be used, but the third surfactant is not limited thereto.

In the step of adding a second surfactant and performing centrifugation, the centrifugation is characterized in that it is performed in the presence of a second surfactant. As the second surfactant, materials which can form micelles in a solution and, due to their size, can induce a difference in concentration between small inter-particle spaces and a bulk solution phase, thereby making them capable of generating osmotic pressure, may be used. As the second surfactant, a known surfactant can be used without limitation as long as it can perform the above-described roles. As the second surfactant, materials the same as or different from the first surfactant and/or the third surfactant described above may be used. Meanwhile, unlike the first surfactant, which does not contain bromide ions, the second surfactant and/or the third surfactant are not limited to the type of ions included therein. For example, BDAC, due to its high aggregation potential, can form micelles with a smaller number of molecules compared to CTAC, exemplified as the first surfactant. Therefore, when benzyldimethyldodecylammonium chloride (BDAC) is used as the second surfactant, a larger number of micelles can be provided in a solution of the same concentration. This indicates that the amount of the second surfactant used can be controlled considering the properties of the chemical species of the selected surfactant.

For example, with respect to the metal nanocube to be finally prepared using the method for preparing the nanocube of the present invention, when the corner radius (CR) value is less than 5 nm or the CSI value is 0.7 or higher, the amount of NaBr to be added determined in the first step (i.e., the amount of NaBr to be added in the second step) may be the number of molecules, which is 200- to 700-fold compared to the surface area value (unit $nm^2$) of the metal nanocube to be finally prepared.

Alternatively, with respect to the metal nanocube to be finally prepared using the method for preparing the nanocube of the present invention, when the corner radius (CR) value is 5 nm or greater or the CSI value is less than 0.7, the amount of the surface-protecting agent to be added determined in the first step (i.e., the amount of NaBr to be added in the second step) is the number of molecules, which is less than 200-fold or in a range of greater than 700- to 10,000-fold compared to the surface area value (unit $nm^2$) of the metal nanocube to be finally prepared.

In a specific embodiment of the present invention, it was confirmed that regardless of the absolute size of the metal nanocube to be finally prepared, when bromide ions were added in an amount of 100 or less or 1,000 or more per unit surface area (i.e., 1 $nm^2$), nanocubes having relatively round edges (i.e., low CSI values) were formed, and when bromide ions were added to be about 390 per 1 $nm^2$, nanocubes having relatively sharpest edges (i.e., having CSI values of about 0.7 to about 0.8, being closer to 1) were formed. However, with regard to small nanocubes with an edge length of 17 nm to 18 nm, when bromide ions were added in an amount of 100 or less or 1,000 or more per unit surface area (i.e., 1 $nm^2$), similarly with particles of other sizes, nanocubes having relatively round edges were formed, and when bromide ions were added to be about 390 per 1 $nm^2$, nanocubes having sharp edges were formed, but the CSI values were low to be in a range of 0.3 to 0.5 due to their small EL values.

The metal nanocube prepared by the method of the present invention may have an average edge length in a range of 15 nm to 300 nm. It has been difficult to prepare nanocubes with a small size of 20 nm or less using the conventional nanocube preparation methods, and in particular, it has been impossible to perform fine-tuning of the shape of these edges.

For example, in the preparation method of the present invention, the first surfactant is preferably used at a concentration of 30 mM to 70 mM relative to the volume of the total solution being used, but the concentration of the first surfactant is not limited thereto. For example, hexadecyltrimethylammonium chloride (CTAC) may be used as the first surfactant, but the first surfactant is not limited thereto.

For example, in the preparation method of the present invention, the reducing agent is preferably used at a concentration of 0.1 mM to 0.5 mM relative to the volume of the total solution being used, but the concentration of the reducing agent is not limited thereto. For example, ascorbic acid may be used as the reducing agent, but the reducing agent is not limited thereto.

For example, in the preparation method of the present invention, the precursor solution containing gold ions is preferably used at a concentration of 0.1 mM to 0.4 mM relative to the volume of the total solution being used, but the concentration of the precursor solution is not limited thereto.

When the concentrations of the reactants are significantly lower or higher than their corresponding ranges, particles of a polyhedral shape may be formed rather than the desired cube-shaped particles.

In each step of the present invention, the materials to be mixed or added may each be mixed or added simultaneously, sequentially, or at different times. For example, the step of preparing the mixed aqueous solution may be performed either by adding metal nanoparticles with an average diameter of 3 nm to 30 nm to a mixed aqueous solution, which contains a first surfactant and a surface-protecting agent in an amount determined according to the step of determining the amount of the surface-protecting agent; or adding a first surfactant and a surface-protecting agent to an aqueous solution containing metal nanoparticles. For example, the step of adding a metal ion precursor may be one in which a reducing agent and a precursor solution containing metal ions are added to the mixed aqueous solution simultaneously, sequentially, or at different times to be reacted.

In addition, the present invention provides a method for preparing a metal nanocube aggregate with a purity of 95% or more, which comprises a step of centrifuging a solution containing metal nanocubes, recovering the precipitate, and redispersing the precipitate in another solution; and a step of adding a second surfactant to the solution and centrifuging the mixture.

As described above, the solution of the redispersion step may further comprise a third surfactant so as to prevent its aggregation, but is not limited thereto.

In addition, the second surfactant is as defined above.

When metal nanoparticles having a certain size or larger are centrifuged in the presence of a second surfactant (e.g., BDAC), osmotic pressure acting against the outside is generated among the particles, which are brought into face-to-face contact, and thereby these particles are compressed and form an aggregate. Therefore, particles of the same size and shape can be refined with a high purity by centrifuging them for a short period of time of 5 to 10 minutes at a rate of a few hundred rpm to 1,000 rpm or less. The principle of this aggregation is illustrated in FIGS. 1$a$ and 1$b$.

Accordingly, a metal nanocube aggregate with a purity of 95% or more can be provided using the refinement method of the present invention, and in particular, the deviation in CSI values of individual nanocubes constituting the metal nanocube aggregate may be within ±10%, but is not limited thereto.

In addition, in the metal nanocube aggregate with a purity of 95% or more provided using the refinement method of the present invention, the deviation in edge length of individual nanocubes constituting the metal nanocube aggregate may be within ±10%, but is not limited thereto.

Specifically, in the metal nanocube aggregate with a purity of 95% or more provided using the refinement method of the present invention, the deviation in both CSI values and edge length of individual nanocubes constituting the metal nanocube aggregate may be within ±10%, but is not limited thereto.

Furthermore, the metal nanocube with a controlled CSI prepared by the method of the present invention; or the high-purity metal nanocube aggregate with an uniform size and shape prepared by the method of the present invention can be used in a probe composition.

Preferably, in the metal nanocube with a controlled CSI prepared by the method of the present invention; or the high-purity metal nanocube aggregate with an uniform size and shape prepared by the method of the present invention, the deviation in both CSI values and edge length is controlled to be within ±10%, and thus, all of the individual nanocubes constituting the metal nanocube aggregate can exhibit uniform physical and/or chemical properties.

As described above, the preparation method of the present invention can provide metal nanocubes with precisely controlled size and shape (e.g., corner sharpness), and furthermore, high-purity metal nanocube aggregates, which comprise metal nanocubes of uniform size and shape with a purity of 95% or more, can be provided using an additional refinement method. Furthermore, since the nanocubes with controlled size and shape can exhibit uniform optical properties that vary according to the size and the edge shape, these nanocubes can be used in an optically detectable probe composition.

In a specific embodiment of the present invention, a series of metal nanocubes with an edge of a sharp or round shape having an edge length in a range of 17 nm to 68 nm or 78 nm were prepared while controlling the size and edge shape of the particles, and it was confirmed that each of these metal nanocubes has a unique optical property according to the size or edge shape. As shown in FIGS. 6a, 6b, 6c, 6d, and 6e, it was confirmed that as the edge length increased (i.e., as the particle size increased), the maximum extinction wavelength appeared in a longer wavelength, whereas even in nanocubes of the same or similar size, as the edge shape became sharper (i.e., having a higher CSI value), the extinction spectrum shifted to a rather long wavelength.

In addition, the metal nanocubes and complexes thereof prepared by the method of the present invention can show various spectroscopic signals (e.g., light absorption, fluorescence, or scattering signals) based on their excellent localized surface plasmon resonance properties, and thus, the metal nanocubes and complexes thereof can be used as probes in various analytical methods.

In a specific embodiment of the present invention, it was confirmed that these particles have an extinction spectrum at various wavelengths (FIG. 6e). In addition, it was confirmed that when a metal nanocube dimer was formed using a self-assembled monolayer (e.g., 1,4-benzenedithiol (BDT)), which was formed on surfaces of the metal nanocubes prepared according to the method of the present invention, as a connecting molecule, a significantly increased surface-enhanced Raman scattering signal (SERS) was shown as a narrow distribution.

The probe composition comprising the metal nanocubes according to the present invention or aggregates thereof may be used for sensors, bioimaging, or therapeutics, but its use is not limited thereto.

In particular, the metal nanocubes according to the present invention or aggregates thereof are specific according to their size and/or edge shape, show optical properties being distinguished from one another, and the signals therefrom have high reproducibility in each particle thereof and/or in repeated experiments, and therefore, they can be effectively used not only for qualitative analysis, but also for multi-analysis that analyzes two or more samples simultaneously, and additionally, for quantitative analysis.

Furthermore, for application in various areas, the metal nanocubes may be surface-modified with appropriate functional groups, polymers, proteins, etc. as necessary, but are not limited thereto.

In addition, since the metal nanocubes according to the present invention are particles with fine-tuned size and shape, they can be used as a building block for forming three-dimensional (3D) nanostructures, metamaterials, optical nanoantennas, etc.

In addition, the present invention provides gold (Au) nanocubes in which each gold nanocube has an average edge length of 20 nm or less.

According to the preparation method of the present invention, it is possible to obtain extremely small-sized gold nanocubes having an edge length at the level of 17 nm to 18 nm, which cannot be obtained by conventional methods. As such, small-sized nanocube particles have a very large volume-to-surface area ratio, which is advantageous in their application in the areas of catalysts, biology, medicine, etc.

The gold nanocubes may be substantially of a cube shape, but they may have some differences in edge length. The average edge length of each gold nanocube may be 20 nm or less, and specifically in a range of 10 nm to 20 nm. In addition, the gold nanocubes may be those in which the deviation in a CSI value of the edge of each gold nanocube is controlled to be within ±10%; or the deviation in edge length of each gold nanocube is controlled to be within ±10%.

One of advantages of the present invention is that not only the preparation method can perform fine-tuning of the size and/or shape, and additionally the degree of corner sharpness of the metal nanocube to be finally prepared by a simple method of controlling the amount of reactants even without a cumbersome additional process, but also can refine the metal nanocube only by an additional process of brief centrifugation in a solution comprising a second surfactant, through which provision of an aggregate of metal nanocubes with uniform size and shape at a purity of 95% or more is enabled, thus making mass-production of metal nanocubes with controlled size and shape and further with controlled optical properties possible.

BRIEF DESCRIPTION OF DRAWINGS

FIG. 1a shows a schematic diagram illustrating selective surface-protection-directed anisotropic growth for sharpness-controlled AuNCs with varied bromide density. The proposed mechanism of modifying reaction kinetics is based on the preferential adsorption of bromide ion to the (100) facet of AuNC. FIG. 1b shows a schematic diagram illustrating synthesized AuNC refinement by centrifugation-driven depletion-induced flocculation in surfactant micelle solutions and subsequent redispersion in DIW. The bottom images show attractive osmotic pressure between AuNCs during the aggregation.

FIG. 3a shows representative TEM images of the AuNCs obtained by adjusting the bromide concentration from 0 mM to 200 mM at a fixed seed amount of a gold precursor. The TEM images correspond to the AuNCs prepared using a bromide concentration of 0 mM, 1 mM, 40 mM, and 200 mM from left to right, respectively. The scale bars indicate 20 nm. FIG. 3b shows the CSI values of the AuNCs of FIG. 3a.

FIGS. 5a and 5b show TEM images illustrating the characterization of shape-controlled AuNCs. FIG. 5a shows TEM images of refined AuNCs prepared using different amounts of seed and bromide, and the insets show representative single-particle images to clearly visualize the difference in sharpness. The numbers in the labels correspond to edge length, and R and S indicate round-cornered AuNCs and sharp-cornered AuNCs, respectively. From left to right, each column was obtained with 300 μL, 9 μL, 6 μL, and 2 μL of a seed solution at the same concentration, respectively. In addition, the bromide concentration was varied at a fixed seed amount to control the corner sharpness, thereby obtaining R AuNCs and S AuNCs. FIG. 5b shows low-magnification SEM images illustrating AuNCs obtained in a high yield after refinement. The scale bars indicate 1 μm.

FIG. 6a shows definitions of edge length (EL), corner radius (CR), and corner sharpness index (CSI). FIG. 6b shows the edge length and the corner radius of a series of AuNCs according to embodiments of the present invention; and FIG. 6c shows the CSIs of a series of AuNCs according to embodiments of the present invention. FIG. 6d shows the calculated number of added bromide ions per AuNC for a series of AuNCs according to embodiments of the present invention. FIG. 6e shows normalized UV-vis spectra for a series of AuNC solutions according to embodiments of the present invention. Solid lines and dashed lines correspond to R AuNCs and S AuNCs, respectively.

FIG. 9a shows dark-field microscope images of individual AuNCs and FIG. 9b shows Rayleigh scattering spectra acquired from 25 different AuNCs and indicated continuously. FIG. 9c shows Rayleigh scattering spectra, which correspond to the data indicated in white dotted line in FIG. 9b. The scale bars in FIG. 9a indicate 0.2 μm. FIGS. 9d to 9f show maximum peak position, scattering intensity at maximum peak, and spectral linewidth according to the size and shape of AuNCs, respectively; and FIG. 9g shows a diagram illustrating the reproducibility of synthesis by three-dimensionally arranging a series of Rayleigh scattering spectra of 53S AuNCs acquired from repeated experiments.

FIG. 10a shows a schematic diagram of the dimer of 78R AuNCs and 72S AuNCs using 1,4-benzenedithiol; FIG. 10b shows a Raman enhancement factor by the formation of a dimer derived by simulation; FIG. 10c shows TEM images of individual dimers; FIG. 10d shows the results of plotting the signals according to the polarization direction of the laser in the dimer; FIG. 10e shows a Raman signal of the corresponding dimer; and FIGS. 10f and 10g show the distribution of Raman enhancement factors measured from 22 individual dimers, which are indicated in a log scale and a linear scale, respectively.

FIGS. 11a and 11b show TEM images. FIG. 11a shows a TEM image of the nanoparticles synthesized on a large scale in Example 3; and FIG. 11b shows a TEM image of the resulting products obtained by a single refinement of a nanoparticle solution having a total volume of 10 mL.

DETAILED DESCRIPTION

Figure 1A:
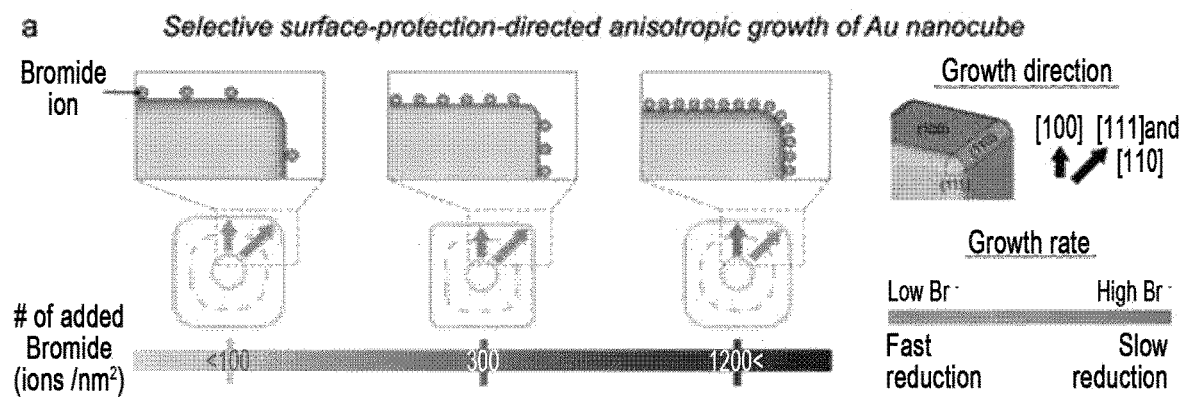
FIGS. 1a and 1b show schematic diagrams illustrating the methods for synthesis and refinement of shape-controlled AuNCs according to the present invention.

Hereinafter, the present invention will be described in more detail with reference to the following Examples. However, these Examples are for illustrative purposes only, and the scope of the invention is not limited by these Examples.

Materials

Hexadecyltrimethylammonium bromide (CTAB), ascorbic acid (AA), and gold chloride trihydrate ($HAuCl_4 \cdot 3H_2O$) were purchased from Sigma-Aldrich. Sodium borohydride was obtained from DaeJung Chemicals & Metals. Hexadecyltrimethylammonium chloride (CTAC) was purchased from Tokyo Chemical Industry (TCI). Deionized water (DIW; Milli-Q, >18.0 MΩ) was used in all of the experiments. All chemicals were used as received without further purification.

Preparation Example 1: Synthesis of Nanosphere Seeds with 10 nm Diameter

CTAC-capped 10 nm gold nanospheres were synthesized according to the protocol disclosed by Zheng, Y. et al. (*Part. Part. Syst. Charact.*, 2014, 31: 266-273). All solutions were prepared based on DIW. First, CTAB-capped seeds with a size of 1 nm to 2 nm were prepared. To synthesize these seeds, 9.75 mL of a 100 mM CTAB solution was mixed with 250 μL of a 10 mM $HAuCl_4$ solution inside a 50 mL round-bottom flask. Subsequently, 600 μL of a freshly prepared ice-cold 10 mM $NaBH_4$ solution was quickly added thereto. The resulting solution was mixed for 3 minutes and stored at 27° C. for 3 hours before the next step. Then, 10 nm gold nanospheres were synthesized with the seeds prepared as described above. 2 mL of 200 mM CTAC, 1.5 mL of 100 mM ascorbic acid, and 50 μL of the previously prepared CTAB-capped seed solution were sequentially mixed inside a 10 mL vial. 2 mL of a 0.5 mM $HAuCl_4$ solution was injected thereinto with a single shot while mixing the solution at a constant speed. The solution was incubated at room temperature for 15 minutes with constant mixing at 300 rpm. Then, the solution was centrifuged twice at 20,600 g for 30 minutes; that is, the solution was first redispersed in DIW (1 mL) and then in a 20 mM CTAC solution (1 mL) for future use.

Example 1: Synthesis of Nanocubes with Controlled Size and/or Shape

The synthesis of nanocubes (NC) was performed in 20 mL glass vials. These vials were cleaned with acetone and DIW before use. In each vial, 100 mM CTAC (6 mL) was mixed with sodium bromide (30 μL) at an appropriate concentration as described in Table 1 below. The previously prepared 10 nm seed solution was diluted to have an OD of 5.6 at 520 nm, and was added thereto in a volume indicated in Table 1 below. A 10 mM ascorbic acid solution (390 μL)

was added thereto and mixed thoroughly. Finally, a 0.5 mM HAuCl$_4$ solution (6 mL) was added thereto with a single shot while mixing the solution at 500 rpm. The resulting solution was incubated with mixing for 19 minutes, and then centrifuged and redispersed in DIW twice.

Example 2: Refinement of Nanocubes

The nanocubes synthesized according to Example 1 were precipitated by centrifugation. The precipitate was redispersed in a 10 mM CTAB solution such that the resulting solution could have a two-fold concentration compared to the original nanocube solution. A calculated amount of the stock solution of benzyldimethyldodecylammonium chloride (BDAC, Sigma-Aldrich) and DIW was added thereto so as to obtain the same nanocube concentration along with an appropriate BDAC concentration for each sample as described in Table 1 below. DIW was added thereto so as to prevent the occurrence of unwanted flocculation.

The solution was mixed and centrifuged according to appropriate conditions. Since 18R and 17S were too small to be aggregated, they were excluded from the purification process. 37R and 32R were centrifuged at 1,000 rpm for 10 minutes. Other samples were centrifuged at 500 rpm for 5 minutes. The supernatants were removed with a micropipette, and the remaining precipitates were redispersed in DIW.

TABLE 1

| Sample | Seed Volume (μL) | Bromide Concentration (mM) | BDAC Concentration (mM) |
|---|---|---|---|
| 18R | 300 | 20 | — |
| 17S | 300 | 120 | — |
| 37R | 30 | 2 | 100 |
| 32S | 30 | 40 | 60 |
| 41R | 9 | 5 | 60 |
| 41S | 9 | 20 | 50 |
| 54R | 6 | 6 | 40 |
| 53S | 6 | 20 | 33 |
| 78R | 2 | 2 | 40 |
| 72S | 2 | 20 | 18 |

Comparative Example 1: Method of Synthesizing Nanoparticles Using CTAB Instead of CTAC, but not Using any Additional Bromide Source Gold nanoparticles were prepared in a similar manner as in Example 1, except that CTAB of the same concentration and volume was used instead of CTAC, and DIW of the same volume was used instead of sodium bromide.

Comparative Example 2: Method of Synthesizing Nanoparticles Using CTAB as Bromide Source, But Not Using CTAC Gold nanoparticles were prepared in a similar manner as in Example 1, except that the same volume of DIW was used instead of CTAC so as to contain CTA in an insufficient amount, and the same volume of 20 mM CTAB was used instead of sodium bromide as a bromide source.

Example 3: Large-Scale Production and Refinement of Nanocubes

Gold nanoparticles were synthesized on a large scale by increasing the scale of the reaction solution based on Example 1. The experimental method used is as follows: the volumes of all of the solutions used in Example 1 were increased by the same factor, but to facilitate the addition of a HAuCl$_4$ solution at once, DIW for dilution into the corresponding volume of 0.5 mM HAuCl$_4$ was added first, followed by the addition of a concentrated 10 mM HAuCl$_4$ solution in a required amount.

As a result, it was confirmed that the gold nanocube synthesis could also be performed in a reaction solution having a volume of 248 mL, which is 20 times the scale of Example 1, and that gold nanocubes of about 10 mg or more could be obtained therefrom. FIG. 11a shows a TEM image of the nanoparticles synthesized on a large scale.

Since nanocubes are nanoparticles that are formed by kinetic control, the control of the reaction rate is a very important factor.

In the existing methods for synthesizing gold nanocubes, there are differences in terms of synthesis yield or shape of the particles depending on the stirring conditions for a reaction solution (i.e., stirring speed, stirring method, etc.), thus resulting in insufficient reproducibility and difficulty in increasing the synthesis scale.

According to the inventors' understanding, existing literature on gold nanocube synthesis has never shown any example with regard to a large-scale gold nanocube synthesis achieved through a synthesis in a reaction solution with a volume of about 50 mL or less, and the amount of the synthesized product and the volume of the reaction solution were limited. However, according to the preparation method of the present invention, nanocubes can be obtained with high reproducibility even when a thorough mixing is performed using a stirring bar, and additionally, uniform nanocubes can be successfully prepared even if the scale is increased by 20 times or more.

In addition, the refinement of nanoparticles in Example 2 can be performed in bulk. In the case of Example 2, the refinement was performed so that the total volume of the mixed solution before centrifugation could be 0.2 mL, but it was confirmed that the refinement was well performed even when the total volume was increased to 10 mL. FIG. 11b shows a TEM image of the resulting products obtained by a single refinement of a nanoparticle solution having a total volume of 10 mL, and from which it was confirmed that the high-purity refinement was well performed even when the scale was increased.

Experimental Example 1: Dark-Field Measurement of Images and Spectra

Dark-field (DF) images were obtained with a 40× objective lens. For 78R and 68S, the exposure time was set at 80 milliseconds, whereas for 41R, the exposure time was set at 120 milliseconds. DF spectra were measured in an inverted microscopy system (Ntegra, NT-MDT). An oil condenser with a numerical aperture (NA) of 1.3 was used for DF measurements. UNPLAN (60×, NA 0.90, air objective) was used for scattering spectra measurements. Cleaned glass was prepared by sonication in acetone and DIW for 5 minutes each. The samples were prepared by drop-casting gold nanocubes (AuNCs) on the cleaned glass followed by spin-coating by microcentrifugation. Spectra were acquired from randomly selected particles observed in DF, with an exposure time of 3 seconds.

Experimental Example 2: Raman Measurement

Samples for Raman measurements were prepared by drop-casting an AuNC solution, mixed with 1,4-benzenedithiol (BDT), on a TEM grid. Raman measurements were performed using an inverted microscopy system (Ntegra, NT-MDT) equipped with UNPLAN (100×, NA 1.3, oil). Particles were identified as a single particle by correlation of the Rayleigh scattering image with the TEM image. Each Raman signal was acquired by exposure on linearly polarized 785 nm lasers (230 µW) for 30 seconds. The signals were detected by a charge-coupled device (CCD) cooled to −70° C. (Andor Newton DU920P BEX2-DD). The enhancement factor was calculated by comparing signals from a 2.5 mM 1,4-benzenedithiol (BDT) bulk solution. The spectra were acquired by exposure on a linearly polarized 785 nm laser (17.6 µW) for 180 seconds using a low-magnification lens (PLAN N, 10×, NA 0.25, air). Differences in lenses were calibrated using the measurement results of 1 mM rhodamine 6G measured with two lenses each. It was assumed that the signals are proportional to the laser power and acquisition time.

The excitation volume is assumed to be cylindrical and the height of the excitation volume was calculated to be 28 fL. One BDT molecule on a thin gold film was assumed to have a molecular footprint of $5.4 \times 10^{-19}$ m$^2$ and a height of $7.6 \times 10^{-19}$ m, and based on this assumption, the enhancement factor (EF) was calculated by the following Equation by calculating the number of molecules in a gap using the volume of the molecule and the volume of the hot spot:

$$EF = \frac{I_{SERS} N_{Bulk}}{I_{Bulk} N_{Gap}}$$

Experimental Example 3: Simulations

Finite element method (FEM) simulations were performed using commercial software (COMSOL) in the scattered-field mode. Linearly polarized plane-wave excitation was used. The nanocube model was based on TEM image analysis.

To create a model similar to the system of the present invention, two modelled nanocubes were placed in parallel, and the gap between the structures was 1.1 nm. Both nanocubes were modelled as gold. The gap length was calculated based on the TEM image analysis. The surrounding medium, including the gap, was modelled in air.

Experimental Example 4: Instruments

TEM and SEM images were obtained by JEM-2100 (JEOL) and Helios NanoLab 650 (FEI) systems, respectively, at the National Center for Inter-University Research Facilities ((NCIRF), Seoul National University, Korea).

Results

Figure 1B:
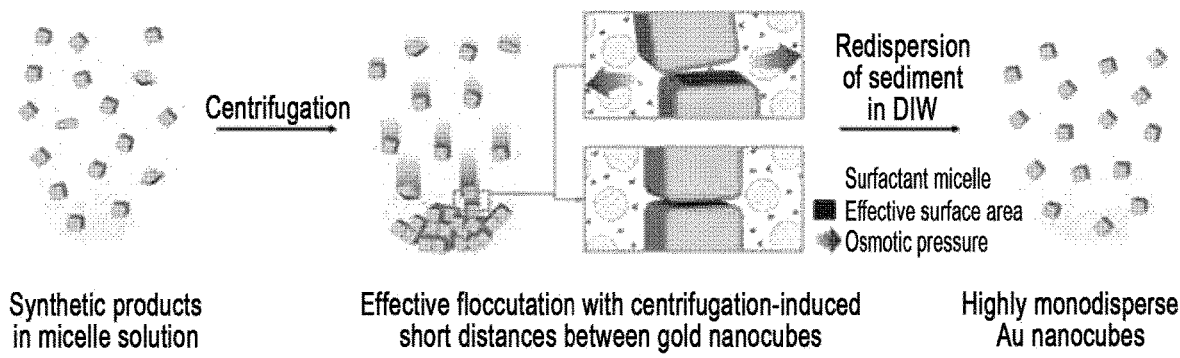

First, selective surface-protection-directed anisotropic growth of AuNCs was performed. Starting from cetyltrimethylammonium chloride (CTAC)-capped gold nanospheres (10 nm), a seed-mediated growth reaction with CTAC, NaBr, and ascorbic acid was conducted at room temperature, and the process is schematically illustrated in FIG. 1a. In this step, the growth kinetics, which depend on bromide concentration, determined the corner sharpness of AuNCs being produced. The growth habits of nanocrystals were determined by the ratio between growth rates of different facets. In order to induce anisotropic growth and create cubic nanostructures, the growth rate along the [100] facet was decreased as the growth rate along the [110]/[111] facet became relatively higher, whereby the (100) facet could be preferentially exposed. Once the amount of bromide was controlled so that the bromide could be favourably adsorbed to the (100) facet, the relative growth rate difference between (100) and the other facets was altered, resulting in forming round-cornered or sharp-cornered AuNCs. When bromide densities were less than 100 ions/nm$^2$, the number of bromide ions was insufficient to completely block the (100) facet. Therefore, the relative growth rate difference between the [100] facet and the [110]/[111] facet was not significantly changed, and thereby round-cornered AuNCs were formed. When a sufficient amount of facet-directing agents (about 350 ions/nm$^2$) was provided, the effective and preferential binding to the (100) facet decreased the reduction rate while the (111)/(110) facet was less affected by bromide ions, and thereby sharp-cornered AuNCs were formed. When the bromide concentration was excessive, they could be adsorbed on the (111)/(110) and (100) surfaces, thereby decreasing the overall growth rate and rate difference between facets. The shape-selective sedimentation of synthesized AuNCs was employed so as to maximize product yields (FIG. 1b). The above method is based on centrifuge-driven depletion-induced flocculation, which consists of the aggregation of AuNCs using surfactant micelles and the reversible redispersion of only the sedimented nanoparticles. When particles were dispersed in the surfactant solution above the critical micelle concentration, exclusion of micelle molecules from the space between AuNCs resulted in osmotic pressure, thereby inducing interparticle aggregation. The aggregation was applied so as to select nanorods or nanobipyramids among mixtures of nanoparticles, and it typically took more than 10 hours to make NPs settle. In the present invention, the sedimentation time was significantly reduced due to brief centrifugation. After centrifuging the nanoparticle solution in the surfactant micelle solution, the inter-particle distance between AuNCs was decreased, and effective aggregation could occur within a very short period of time. Since the attractive force between two particles is proportional to the surface areas facing each other, nanocubes (NCs) with flat surfaces are advantageous compared to those with curved surfaces (e.g., rods) or with smaller faces (e.g., bipyramids). In the present invention, it was possible to achieve AuNC yields of 95% or above by adjusting the micelle concentration to selectively induce AuNC aggregation.

Figure 2A:
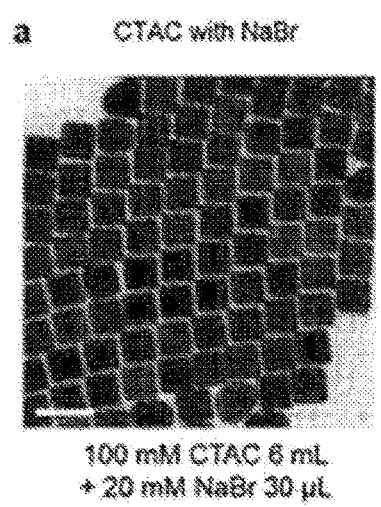
FIGS. 2a, 2b, and 2c show TEM images illustrating the shapes of AuNCs according to an embodiment of the present invention and nanoparticles according to Comparative Examples 1 and 2. The scale bars indicate 100 nm.
Figure 2B:
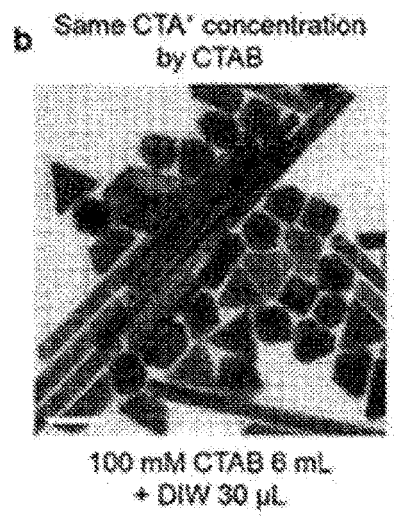
Figure 2C:
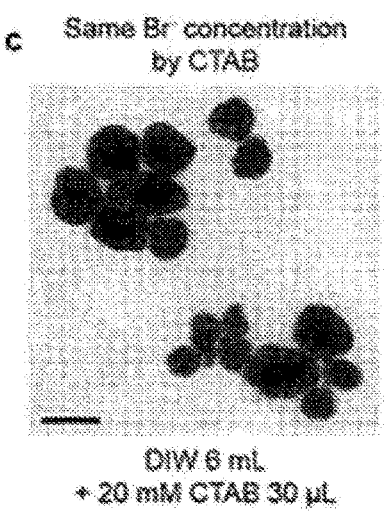

In addition, the roles of each component used in the method of preparing the AuNCs according to the present invention, in which the shape and/or corner sharpness are controlled, were confirmed. For this purpose, AuNCs were prepared by the method of Example 1 as an experimental group using 100 mM CTAC (6 mL) and 20 mM sodium bromide (30 µL) as a source of bromide ions. Furthermore, the shapes of the nanoparticles prepared in Comparative Example 1 as a comparative group, in which a sufficient amount of a surfactant was used but CTAB (containing bromide instead of chloride) was used in the same amount, and DIW was used instead of a sodium bromide solution as an additional source of bromide ions; and the shapes of the AuNCs and nanoparticles prepared under the above-described three conditions were observed by SEM, and the results are shown in FIGS. 2a, 2b, and 2c. As shown in FIG. 2a, the AuNCs according to the present invention prepared using a sufficient amount of a surfactant (i.e., CTAC) and a small amount of sodium bromide were uniformly prepared in the form of cubes. However, in the case of Comparative Example 1, where nanoparticles were prepared using a sufficient amount of a surfactant (i.e., CTAB instead of CTAC) and bromide ions, although individual particles showed certain crystal shapes, the shape and size of these particles were not uniform, and a particle mixture where particles (e.g., nanorods, nanoprisms, etc. (instead of nanocubes)) were mixed was formed as shown in FIG. 2b, and it was difficult to refine high-purity nanocubes therefrom. Furthermore, when CTAB was added at the same concentration level as the bromide which was provided by sodium bromide in Example 1 (i.e., in the case of Comparative Example 2, where the surfactant was used at a significantly low concentration), as shown in FIG. 2c, irregular nucleation occurred in the solution as well as on the surface of the seed particles and formed a mixture of amorphous particles in which both size and shape were not defined.

Figure 3A:
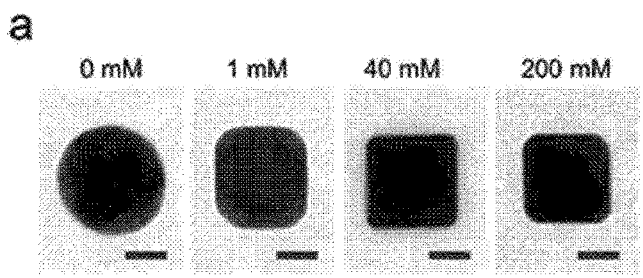
FIGS. 3a and 3b show images illustrating nanocubes prepared by adjusting the shape and/or corner sharpness by a method according to an embodiment of the present invention.
Figure 3B:
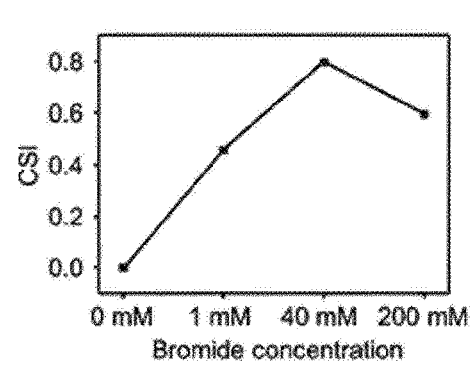
Figure 4:
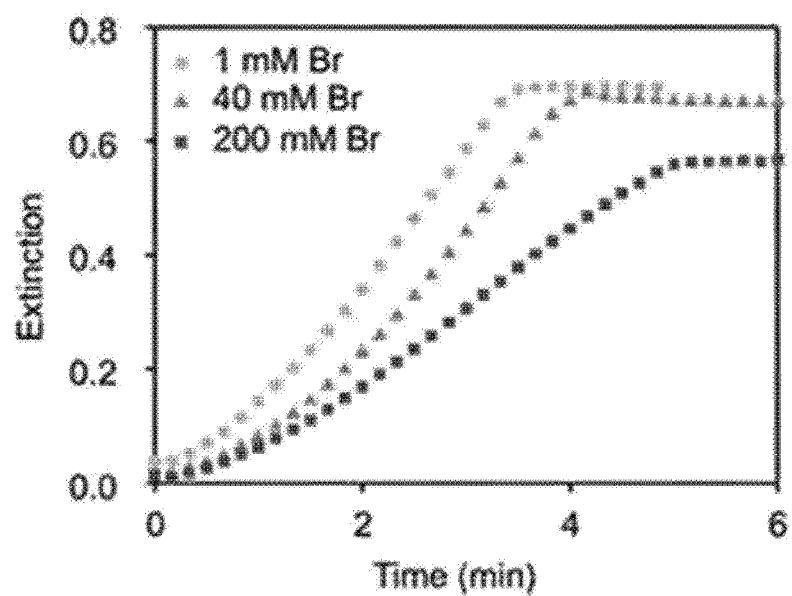
FIG. 4 shows a graph illustrating bromide-concentration-dependent growth kinetics obtained using a UV-vis spectrophotometer.

Furthermore, it was confirmed in the present invention that corner sharpness can be fine-tuned. AuNCs with different corner sharpnesses were obtained with varying bromide concentrations from 0 mM to 200 mM (FIGS. 3a and 3b). With increasing bromide concentration, the corner sharpness increased first and then decreased. The size of AuNCs was slightly decreased at the highest bromide concentration because the number of by-products had increased. To study the mechanism of corner sharpness control, the present inventors have explored the growth kinetics during shape evolution by UV-vis spectroscopy. The bromide concentration was varied while maintaining the same amounts of CTAC, seed, and ascorbic acid (AA). After adding gold precursors, the changes in extinction intensity were monitored at 10-second intervals at each maximum localized surface plasmon resonance (LSPR) wavelength (i.e., 544 nm in the condition of 1 mM NaBr; 560 nm in the condition of 40 mM NaBr; and 556 nm in the condition of 200 mM NaBr) of the fully grown structure (FIG. 4). The slow increase of extinction for 200 mM indicates that increasing the bromide concentration disrupts reduction, supporting the synthesis mechanism proposed in FIG. 1a. In the present invention, it was confirmed that only the introduction of seeds initiates the growth event; therefore, additional nucleation without seeds was not detected in UV-vis measurement.

Figures 6A, 6B, 6C, 6D, 6E:
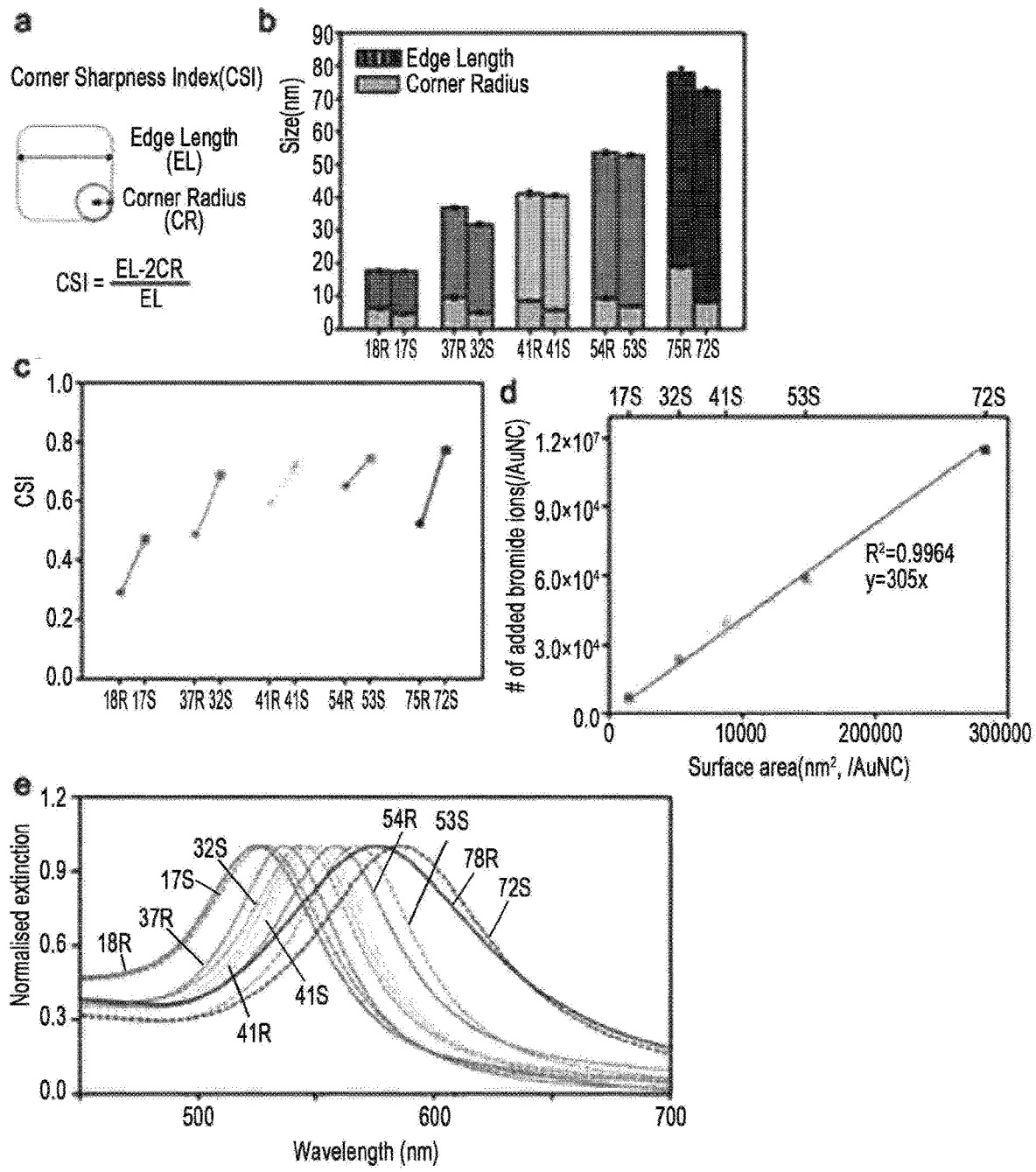
FIGS. 6a, 6b, 6c, 6d, and 6e show drawings illustrating the characterization of shape-controlled AuNCs.
Figure 7A:
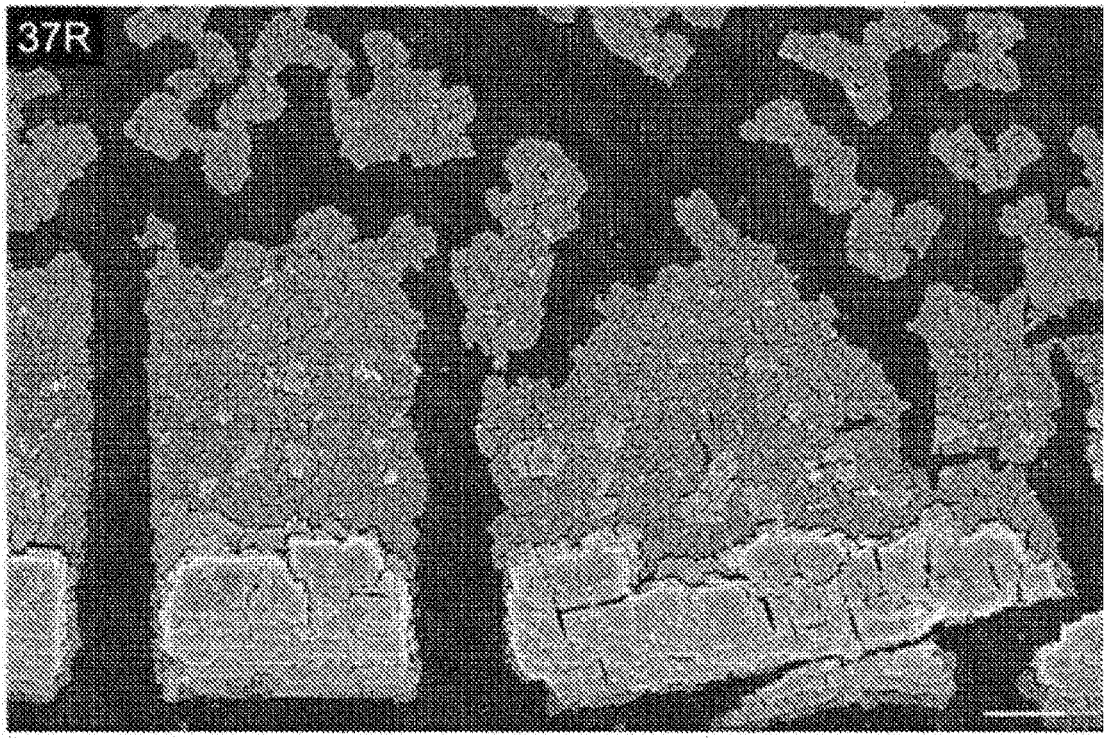
FIG. 7a shows low-magnification SEM images of 37R AuNCs and 32S AuNCs. The scale bars indicate 1 μm.
Figure 7A:
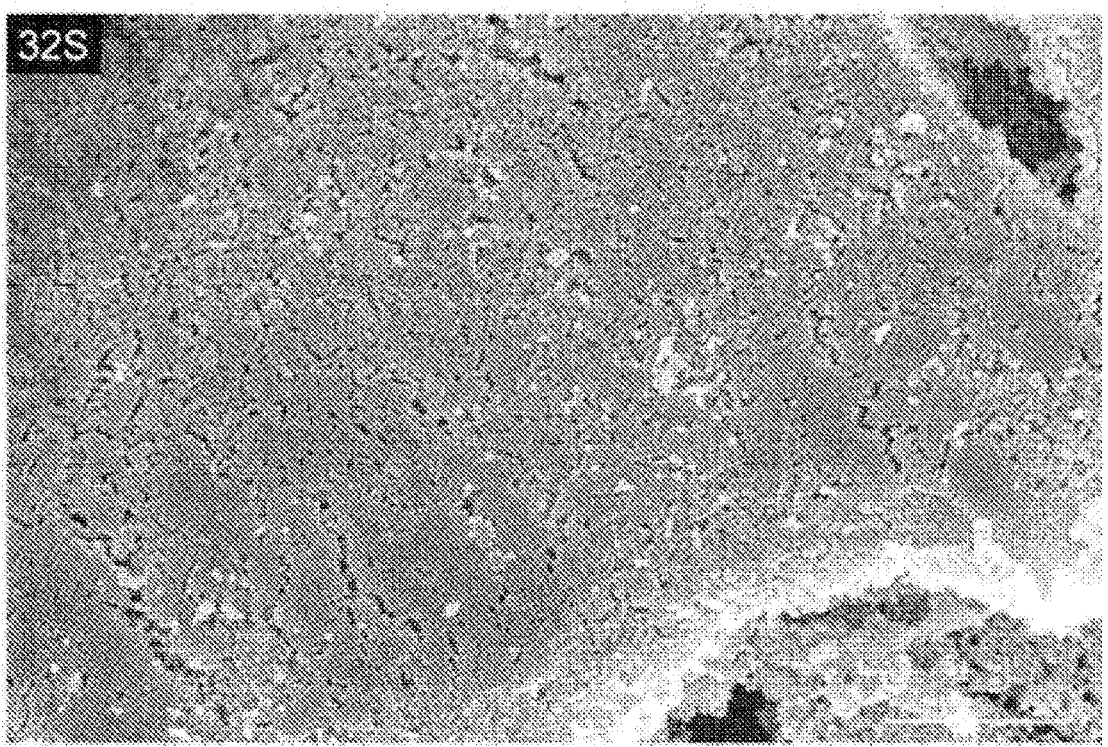
Figure 7B:
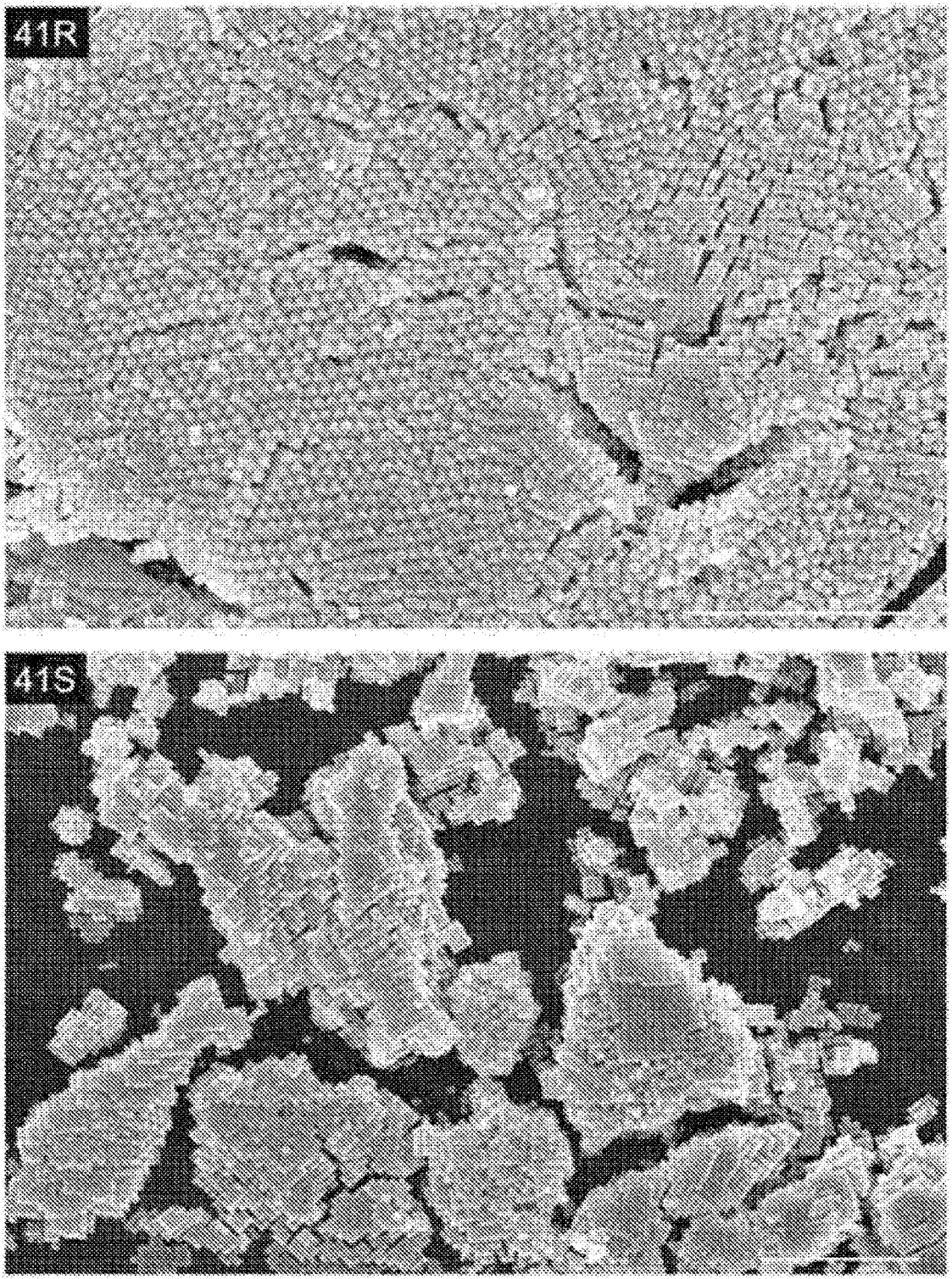
FIG. 7b shows low-magnification SEM images of 41R AuNCs and 41S AuNCs. The scale bars indicate 1 μm.
Figure 7C:
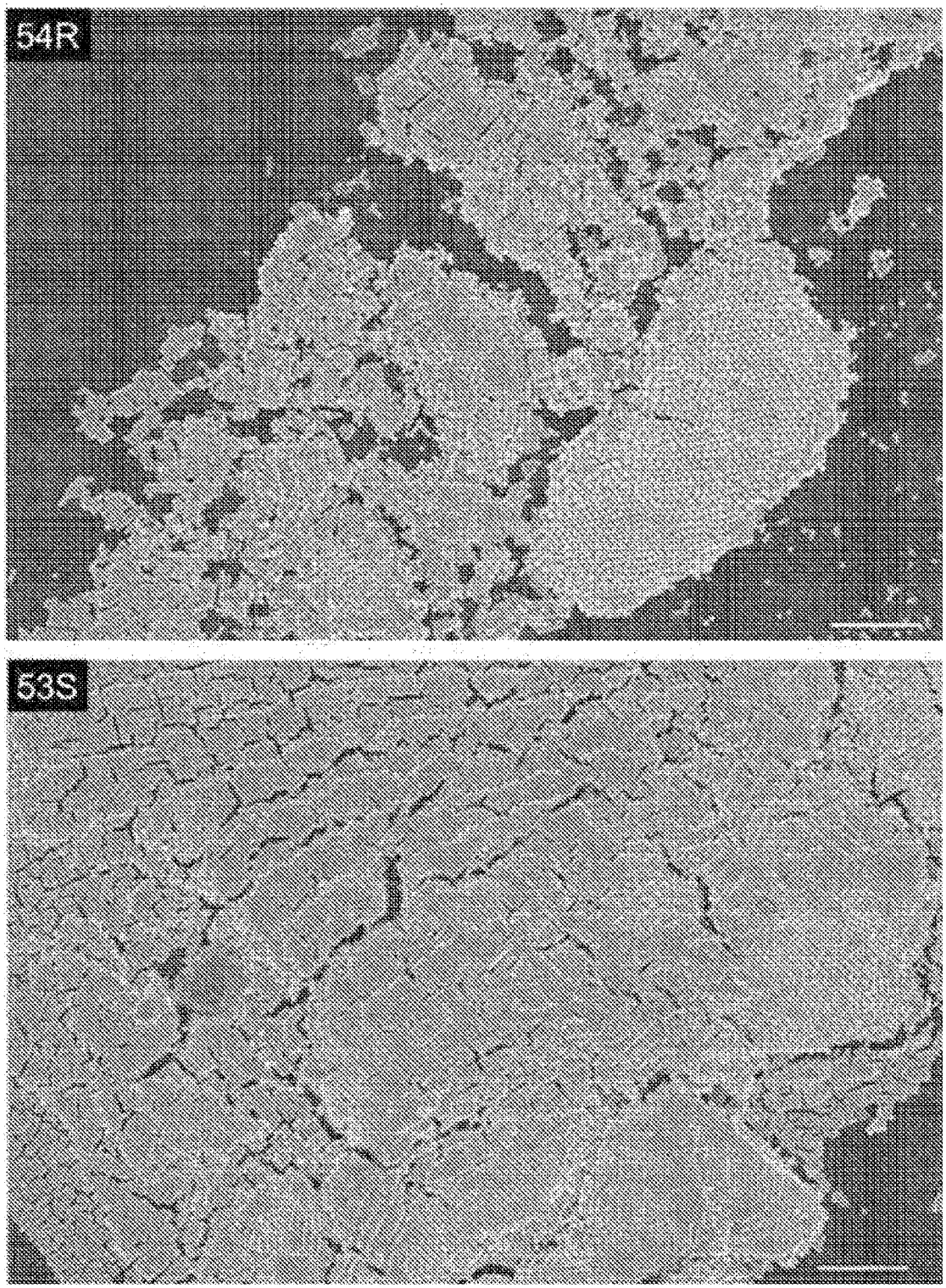
FIG. 7c shows low-magnification SEM images of 54R AuNCs and 53S AuNCs. The scale bars indicate 1 μm.
Figure 7D:
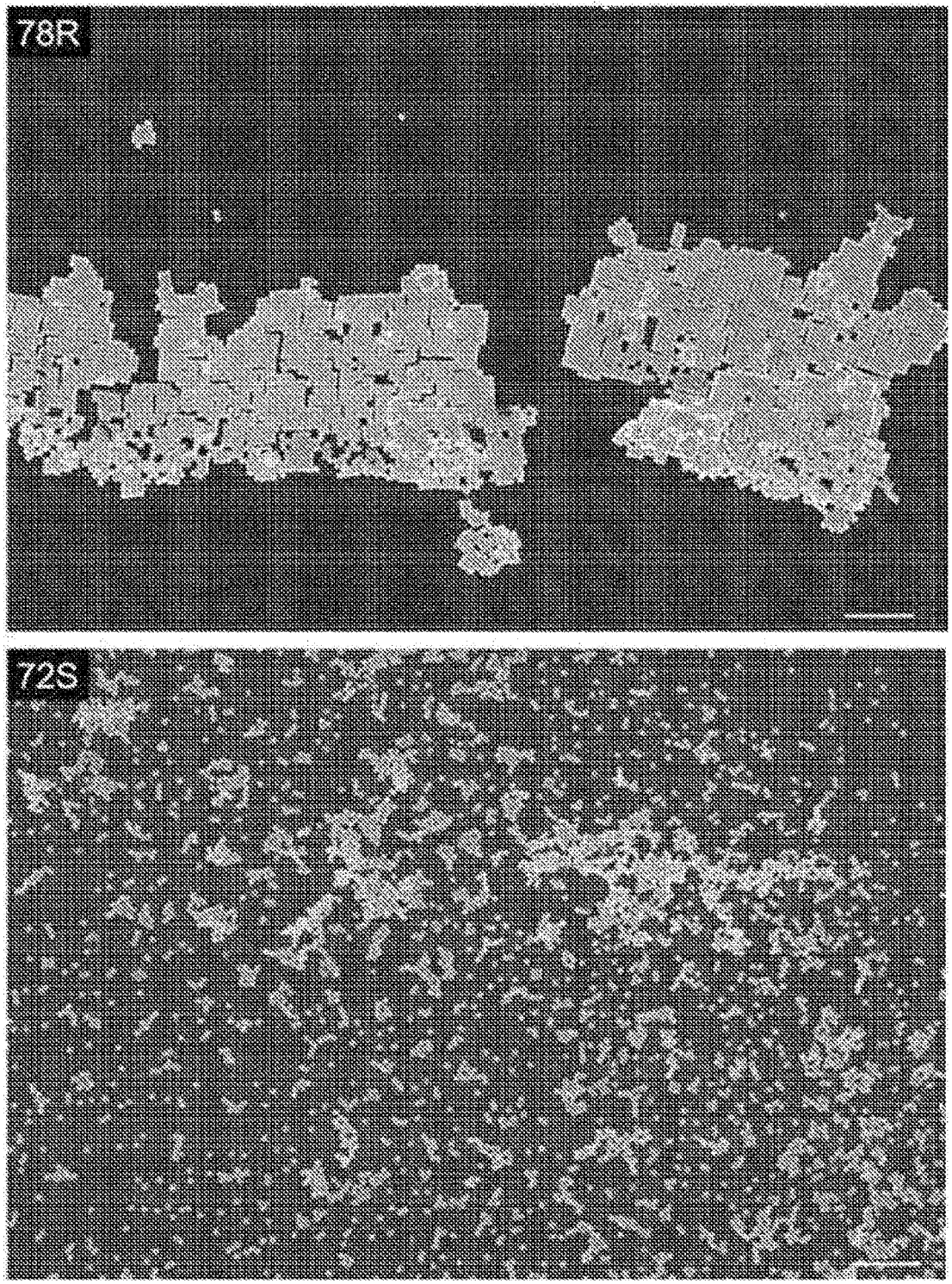
FIG. 7d shows low-magnification SEM images of 78R AuNCs and 72S AuNCs. The scale bars indicate 1 μm.

To substantiate the above principle, the present inventors have adopted simultaneous control of the size and corner sharpness by changing the amounts of seed and bromide. The amount of seed was adjusted by the volume of a seed solution (e.g., 300 μL, 30 μL, 9 μL, 6 μL, and 2 μL). In addition, the concentration of bromide was varied so as to control the corner sharpness at a fixed amount of seed. A lower density of bromide was applied to produce round-cornered AuNCs. As the overall size decreased, the concentration of bromide added to yield AuNCs decreased. This result is due to the decrease in the number of particles, although the surface area increased significantly with larger AuNCs. Following the preparation, the AuNCs were dispersed in a BDAC solution and centrifuged for 5 to 10 minutes. Since aggregation force has a positive correlation with the overlaid surface area between nanoparticles and micelle concentration, the concentration required for aggregation decreased as AuNCs became larger. TEM images show different sizes of refined AuNCs, and the insets show representative images to clearly visualize structural variations (FIG. 5a). Each column represents the result of adjusting the amount of seed, and the top and bottom rows correspond to round-cornered AuNC and sharp-cornered AuNC, respectively. To analyze the structural features of each AuNC based on the TEM images, edge length was defined as the distance between the two ends of AuNCs and corner radius as the radius of the circle that perfectly matches with the corner curvature (FIG. 6a). Numbers indicated in the samples represent the edge length, and R and S correspond to round-cornered nanocubes (NCs) and sharp-cornered nanocubes (NCs), respectively. After the refinement, the yield was improved to 95% or higher for all of the AuNCs except the smallest (larger SEM images in FIG. 5b and FIG. 7). The 32S AuNCs were shown to have similar aggregation potentials to by-products of gold nanorods, providing yields of about 95%. The yields acquired for other AuNCs exceeded 97% (n>400). It was difficult to find an appropriate surfactant to make the smallest aggregate due to their low surface area. With decreasing seed volume, the edge length increased from 17 nm to 78 nm. The corner radius was plotted in FIG. 7b so as to intuitively show the sharpness. The synthesis of AuNCs smaller than 25 nm using solution methods was not expected to be possible because the self-diffusion coefficient of gold atoms (3 nm to 12 nm) is higher than those of other metals such as platinum (0.3 nm to 1 nm), inhibiting the effective exposure of the (100) facet by promoting the movement of gold atoms from higher-energy (111) to lower-energy (100). Nevertheless, AuNCs with an edge length of 17 nm were successfully synthesized by the method of the present invention. This is the smallest size for AuNCs known to date.

Figure 8:
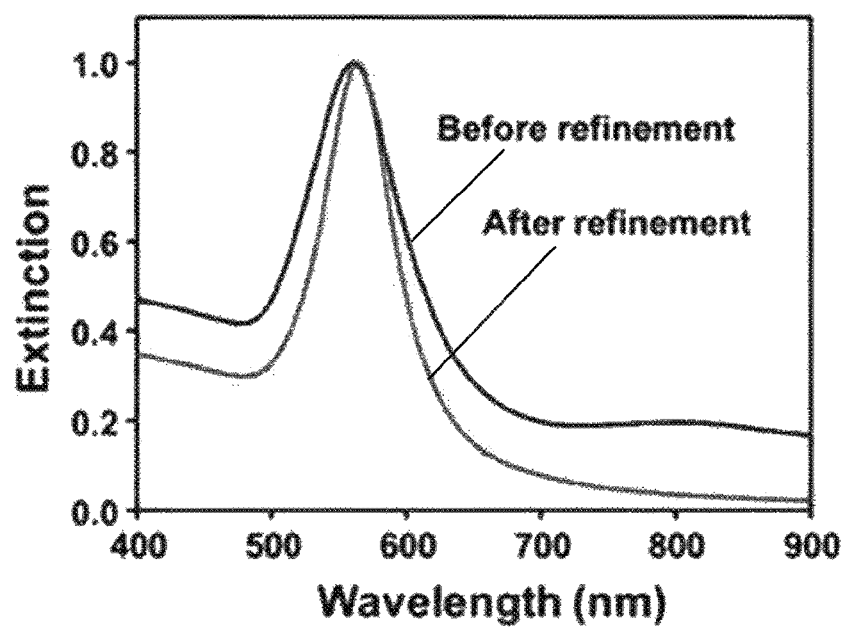
FIG. 8 shows a graph illustrating representative extinction spectra before and after refinement for 50R AuNCs.

The present inventors have proposed the term "corner sharpness index (CSI)" to characterize sharpness regardless of edge length. The method of defining the CSI is schematically shown in FIG. 6a. Sharper nanocubes (NCs) have CSI values closer to 1. While the CSI values of four large, sharp-cornered AuNCs were similar, the CSI value of 17S was lower than those of others (FIG. 6c). A reasonable explanation for this was the relatively high surface tension due to the small size of 17S. To provide stoichiometry information for sharp-cornered AuNCs, the number of bromide ions required per AuNC was calculated (FIG. 6d). This was not the number of ions adsorbed on the surface, but rather corresponded to the number of ions added. The linear relationship between surface area and the number of bromide ions added reveals a uniform density of bromide ions of about 390 ions/$nm^2$, regardless of size. This result provided a rough estimate of the number of bromide ions required for the formation of sharp-cornered AuNCs with a specific size. Normalised UV-vis spectra for a series of AuNC solutions showed a gradual red-shift as the corner became more sharpened and as the edge length increased due to the retardation effect (FIG. 6e). Narrower spectral bandwidths after refinement indicate highly monodisperse AuNCs (FIG. 8).

Figures 9A, 9B, 9C, 9D, 9E, 9F, 9G:
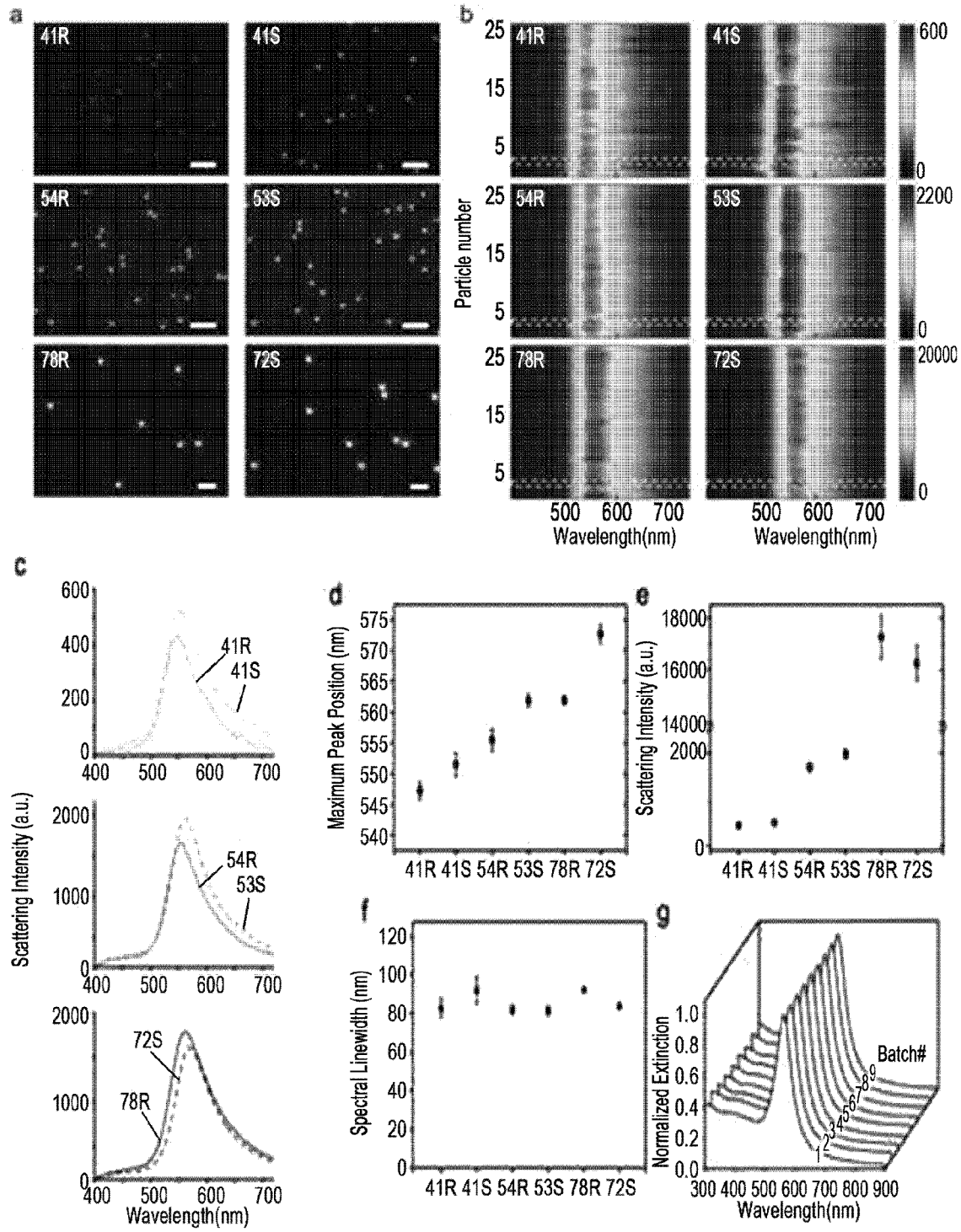
FIGS. 9a, 9b, 9c, 9d, 9e, 9f, and 9g show drawings illustrating the results of far-field scattering analysis of AuNCs at the single-particle level.

In the present invention, it was noted that optical properties of AuNCs can be tuned by adjusting their structures. The Rayleigh scattering signal was measured at the single-particle level using a dark-field (DF) microscope and the results are shown in FIG. 9a. As shown in FIGS. 9a, 9b, 9c, 9d, 9e, 9f, and 9g, the DF micrographs (FIG. 9a) and scattering spectra (FIG. 9b) obtained from 25 AuNCs exhibited a uniform scattering property. Consistent spectra were obtained for each of the 25 particles because of the narrow distribution and high yield of AuNCs, and the averaged representative spectra are shown in FIG. 9c. In addition, the maximum peak positions obtained from the scattering spectrum measured for a series of AuNCs, in which the size (i.e., edge length) and/or shape were different, and scattering intensities at the peak positions are shown in FIGS. 9d and 9e, respectively. As shown in FIGS. 9d and 9e, the positions and intensities of the maximum scattering wavelength varied according to the size and/or edge shape of the AuNCs. These results indicate that in similar-sized AuNCs, as the corner sharpness became higher, the scattering signal increased, and the average peak position was shifted to a long wavelength. This may be mainly attributed to the retardation effect due to large size. In particular, a slightly reduced scattering intensity was observed in 72S despite its higher corner sharpness compared to 78R, and this was thought to have occurred because the Rayleigh scattering generally increases in proportion to the square of the volume, and thus, the scattering-increasing effect was compounded in 78R, which has a large volume.

Meanwhile, the spectrum of each AuNC is shown in FIG. 9f along with its linewidth. As shown in FIG. 9f, it was confirmed that these AuNCs have a scattering spectrum of uniform linewidth regardless of their size or shape. Furthermore, 53S AuNCs having the same size and corner shape were synthesized in several batches, and the Rayleigh scattering spectra of the AuNCs obtained from each batch were measured, and a comprehensive spectral profile is three-dimensionally shown in FIG. 9g. As shown in FIG. 9g, the Rayleigh Raman spectra measured from the AuNCs produced in several different batches were all consistent, indicating that if the synthesis method of the present invention is used, uniform AuNCs can be produced regardless of the batch.

Figures 10A, 10B, 10C, 10D, 10E, 10F, 10G:
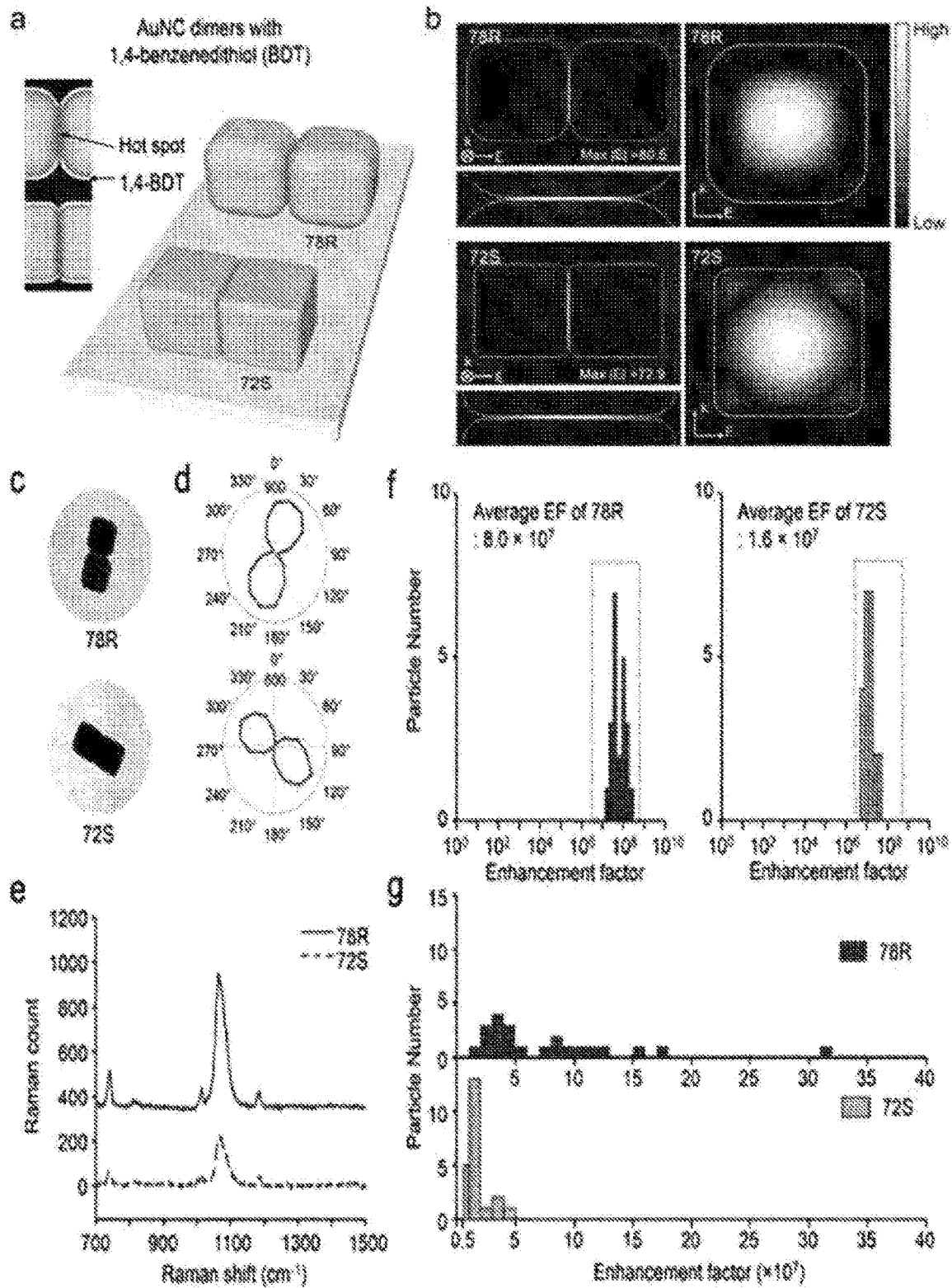
FIGS. 10a, 10b, 10c, 10d, 10e, 10f, and 10g show drawings illustrating the results of single-particle SERS analysis for the plasmonic nanogap between the nanocubes in a dimer of 78R AuNCs and 72S AuNCs.

Finally, in the present invention, structural effects were studied on near-field enhancement by surface-enhanced Raman scattering (SERS) with 78R and 72S. Specifically, a self-assembled monolayer of BDT was formed on the surface of AuNCs, and these were then assembled into an AuNC dimer. The shape of the formed AuNC dimer is schematically shown in FIG. 10a. FIG. 10c shows TEM images of dimers of 78R and 72S, respectively. Each of the 22 individual dimers was analyzed and confirmed to have an average gap size of 1.1 nm (within 10% deviation). It was confirmed from the polar plot of the Raman signal prepared while changing the polarization angle of the laser of irradiation that the maximum Raman signal enhancement was large in the long-axis resonance mode of the dimer and/or in 78R. In the present invention, the Raman enhancement factor of the dimer prepared using BDT was calculated to be $8.0 \times 10^7$ in 78R and $1.6 \times 10^7$ in 72S (FIGS. 10f and 10g). This tendency is also consistent with the simulation results shown in FIG. 10b. This indicates that the control of corner sharpness is a factor capable of controlling optical properties of dimers as well as in single particles. In contrast, the 72S dimer showed a narrower distribution of spectrum compared to the 78R dimer, and this is thought to be because the 72S dimer has a smaller corner radius deviation than the 78R, thus resulting in higher homogeneity, and this was supported by the fact that the standard deviation of the measured corner radius of 78R was 1.9 times larger than that of 72S. This pattern also appeared in AuNCs with a different size.

In conclusion, the present invention proposes a method for producing metal nanocubes in high yield while precisely controlling their size and corner sharpness. The present invention provides a straightforward method of size control by tuning the ratio between the amount of a seed and a precursor, as well as corner sharpness control by varying the amount of bromide ions being added. From stoichiometric information, once the size of a metal nanocube is selected, the bromide concentration required for round-cornered metal nanocubes or sharp-cornered metal nanocubes can easily be determined. The centrifuge-driven aggregation of the synthesized metal nanocubes is simple and feasible for shape-selective nanoparticle refinement, and can be extended to any type of nanoparticle mixture without intricate preparation.

The precise shape control of metal nanocubes enables effective fine-tuning of far-field and near-field responses, thereby allowing conversion of structural distinctions to the modulation of optical properties. Therefore, based thereon, it is expected that practical and scalable synthesis of metal nanocubes with the potential for use as a basic nanostructure for synthesis or for self-assembly as 2D or 3D materials may be realized and a method capable of a large-scale synthesis thereof may be developed. Furthermore, applications with highly enhanced plasmonic properties, which are achieved through the precisely controlled design of novel nanostructures, may be expected.

The invention claimed is:

1. A method for preparing a plurality of metal nanocubes, the method comprising:
(a) selecting an edge length, a surface area (in nm²), and a corner sharpness of the metal nanocubes to be prepared, wherein the corner sharpness is defined by a corner radius (CR) value, a corner sharpness index (CSI) value, or both,
wherein the edge length (EL) is the shortest distance from one point of a flat surface of a metal nanocube to a point on another parallel surface,
wherein the corner radius (CR) value is the size (in nm) of a radius of a circle that perfectly matches a curvature of a corner of the metal nanocube,
wherein the corner sharpness index (CSI) value is defined by Equation 1, below—

$$CSI \equiv \frac{EL - 2CR}{EL} \qquad \text{Equation 1}$$

wherein the edge length selected is in the range of from 15 to 300 nm, and
wherein the metal is gold (Au);
(b) mixing a first surfactant, a surface-protecting agent, and gold metal nanoparticles together to provide a mixed aqueous solution,
wherein the surface-protecting agent is NaBr and the amount of NaBr used to form the mixed aqueous solution is determined based on the surface area of the metal nanocubes to be prepared selected in step (a) and the corner radius (CR) value or the corner sharpness index (CSI) value of the metal nanocubes to be prepared selected in step (a),
wherein, when the CR value selected in step (a) is less than 5 nm or the CSI value selected in step (a) is 0.70 or higher, the mixing of step (b) comprises adding an amount of NaBr so that the ratio of bromine atoms in the mixed aqueous solution to the surface area of the metal nanocubes to be prepared selected in step (a) is in the range of from 200 to 700,
wherein, when the CR value selected in step (a) is 5 nm or higher or the CSI value selected in step (a) is less than 0.70, the mixing of step (b) comprises adding an amount of NaBr so that the ratio of bromine atoms in the mixed aqueous solution to the surface area of the metal nanocubes to be prepared selected in step (a) is less than 200 or is in the range of greater than 700 to 10,000, wherein the first surfactant is added to the mixed aqueous solution in an amount in the range of from 30 mM to 70 mM, based on the total volume of the mixed aqueous solution, and wherein the gold metal nanoparticles added to the mixed aqueous solution have an average diameter of from 3 nm to 30 nm;

wherein the gold metal nanoparticles added to the mixed aqueous solution have an average diameter of 3 nm to 30 nm;

(c) adding a metal ion precursor solution and a reducing agent to the mixed aqueous solution formed in step (b) to provide a reaction solution, wherein the reducing agent is ascorbic acid and wherein the reducing agent is added to the reaction solution in an amount in the range of from 0.1 mM to 0.5 mM, based on the total volume of reaction solution, wherein the precursor solution comprises gold metal ions, wherein the surface-protecting agent binds specifically to a (100) facet of a metal nanocube so as to control its crystal growth from a corresponding surface;

(d) centrifuging the reaction solution formed in step (c) to provide a solid precipitate and redispersing at least a portion of the solid precipitate in another solvent to form a second solution; and (e) adding a second surfactant to the second solution to provide a final solution and centrifuging the final solution to obtain an aggregate of gold metal nanocubes.

2. The method of claim 1, wherein the metal nanocubes recovered in step (e) have a purity of 95% or higher with a deviation in edge length of within ±10%.

3. The method of claim 1, wherein the adding of step (c) comprises adding the reducing agent and the metal ion precursor solution comprising gold metal ions to the mixed aqueous solution simultaneously, sequentially, or at different times.

* * * * *